(12) United States Patent
Wang

(10) Patent No.: US 7,516,873 B2
(45) Date of Patent: Apr. 14, 2009

(54) FLUID DISPENSING OR FEEDING DEVICE

(76) Inventor: Samw Hong Jen Wang, No. 14-3, Fusing 1st Road, Singing District, Kaohsiung 80053 (TW)

( * ) Notice: Subject to any disclaimer, the term of this patent is extended or adjusted under 35 U.S.C. 154(b) by 78 days.

(21) Appl. No.: 11/827,584

(22) Filed: Jul. 11, 2007

(65) Prior Publication Data

US 2007/0257065 A1    Nov. 8, 2007

Related U.S. Application Data

(63) Continuation-in-part of application No. 10/986,416, filed on Nov. 10, 2004, now Pat. No. 7,455,658.

(51) Int. Cl.
*B65D 88/54*    (2006.01)
(52) U.S. Cl. .................. 222/333; 222/386; 222/529; 604/85; 604/251
(58) Field of Classification Search ............. 222/333, 222/386, 529; 604/85, 251
See application file for complete search history.

(56) References Cited

U.S. PATENT DOCUMENTS

| | | | | |
|---|---|---|---|---|
| 2,675,946 A * | 4/1954 | Strempel | ............. | 222/137 |
| 2,850,211 A | 9/1958 | Fernandez | | |
| 3,227,173 A | 1/1966 | Bernstenin | | |
| 4,187,890 A * | 2/1980 | Stach et al. | ............. | 141/27 |
| 4,369,664 A * | 1/1983 | Bunce et al. | ........... | 73/864.12 |
| 4,519,792 A * | 5/1985 | Dawe | ............. | 604/152 |
| 5,014,884 A * | 5/1991 | Wunsch | ............. | 222/333 |
| 5,295,890 A * | 3/1994 | Myers | ............. | 446/176 |
| 7,216,782 B2 | 5/2007 | Sugimura et al. | ....... | 222/260 |
| 7,455,658 B2 * | 11/2008 | Wang | ............. | 604/85 |
| 2004/0182887 A1 * | 9/2004 | Sugimura et al. | ....... | 222/386 |
| 2006/0249541 A1 * | 11/2006 | Wang | ............. | 222/333 |

* cited by examiner

*Primary Examiner*—Frederick C. Nicolas
(74) *Attorney, Agent, or Firm*—Charles E. Baxley

(57) ABSTRACT

A fluid dispensing device includes a fluid bottle, a discharge tube, a pressurizing device coupled between the bottle and the discharge tube for forcing the fluid to flow through the discharge tube without gravity, the pressurizing device includes a container coupled between the bottle and the discharge tube, a piston is slidably received in the container, and a motor is coupled to the piston to move the piston in the reciprocating action within the container, and a speed reduction device is coupled between the motor and the piston for allowing the piston to be actuated by the motor with a reduced driving speed and an increased driving torque.

5 Claims, 3 Drawing Sheets

FLUID DISPENSING OR FEEDING DEVICE

The present invention is a continuation-in-part of U.S. patent application Ser. No. 10/986,416, filed 10 Nov. 2004 now U.S. Pat. No. 7,455,658.

BACKGROUND OF THE INVENTION

1. Field of the Invention

The present invention relates to a fluid dispensing or feeding device, and more particularly to a fluid dispensing or feeding device including a pressurizing device for pressurizing fluid and for allowing fluid bottle to be disposed below hearts of patients or users, and thus for allowing the fluid dispensing or feeding device to be easily carried by the patients or users.

2. Description of the Prior Art

Typically, fluid dispensing or feeding devices have been developed and provided for feeding or injecting medicinal fluids intravenously into human body tissue, and comprise a feed tube having a hypodermic needle provided on one end thereof for engaging into a fluid bottle or container, and having an injection needle provided on the other end thereof, for penetrating into patient's body tissue and for the purposes of injecting the fluid as desired.

The flow of the fluid from the bottle is normally actuated by the gravity and is regulated by a clamp valve on the flexible outlet tube so as to control the dispensing of the fluid. Also positioned in the discharge line and located near the bottle is a drip meter or flow indicating device usually made of transparent material for allowing the drops of fluid passing from the bottle to the tubes may be observed.

For example, U.S. Pat. No. 2,850,211 to Fernandez, and U.S. Pat. No. 3,227,173 to Bernstein disclose two of the typical fluid dispensing or feeding devices, which also include a bottle or container for receiving the medicine fluid therein, and arranged for allowing the medicine fluid to flow into patient's body tissue by gravity, and which comprise safety valves for limiting the flow of the fluid, and for preventing the fluid from flowing backward to the bottle.

Normally, the fluid bottle or container is required to be held or supported above the heart of the patient, for allowing the fluid to suitably flow into patient's body tissue by gravity. Once the fluid bottle or container is disposed below the heart of the patient, the fluid may no longer suitably flow into patient's body tissue by gravity.

However, it is inconvenient for the users, particularly the patient to support the fluid bottle or container above the heart of the patient, such that the patients are normally confined or prohibited from going too far from hospitals.

U.S. Pat. No. 7,216,782 to Sugimura et al. discloses one of the typical dispensers for discharging liquid material and comprising a pulse motor for actuating or driving a plunger and for forcing and dispensing or discharging the liquid material out through a nozzle.

However, the pulse motor is directly coupled to the plunger for directly operating and actuating the plunger, and no speed reduction devices or mechanisms may be provided and coupled between the pulse motor and the plunger for suitably coupling the pulse motor to the plunger and for allowing the plunger to be suitably actuated or driven by the pulse motor with a reduced driving speed and/or an increased driving torque.

The present invention has arisen to mitigate and/or obviate the afore-described disadvantages of the conventional fluid dispensing or feeding devices.

SUMMARY OF THE INVENTION

The primary objective of the present invention is to provide a fluid dispensing or feeding device including a pressurizing device for pressurizing fluid and for allowing fluid bottle to be disposed below hearts of patients or users, and thus for allowing the fluid dispensing or feeding device to be easily carried by the patients or users.

The other objective of the present invention is to provide a fluid dispensing or feeding device including a speed reduction device or mechanism coupled between the motor and the piston for allowing the piston to be actuated or driven by the motor with a suitably reduced driving speed and/or a suitably increased driving torque.

In accordance with one aspect of the invention, there is provided a fluid dispensing device comprising a bottle for receiving fluid therein, a discharge tube, a pressurizing device coupled between the bottle and the discharge tube for pressurizing the fluid and for forcing the fluid to flow through the discharge tube without gravity, the pressurizing device including a container coupled between the bottle and the discharge tube, a piston slidably received in the container, and a motor coupled to the piston to move the piston in the reciprocating action within the container, and a speed reduction device coupled between the motor and the piston for allowing the piston to be actuated by the motor with a suitably reduced driving speed and/or with a suitably increased driving torque.

The container includes a shaft rotatably supported in the container and extended into the container, and an eccentric crank coupled to the shaft and coupled to the piston for allowing the crank and the piston to be rotated or driven by the shaft and the motor and the speed reduction device.

The speed reduction device includes a first pinion attached to a spindle of the motor and coupled to the shaft for allowing the shaft to be driven by the motor.

The speed reduction device includes a pole rotatably supported in the container, a first gear attached to the pole and engaged with the first pinion, a second gear attached to the shaft, and a second pinion attached to pole and engaged with the second gear of the shaft for allowing the shaft to be rotated and driven by the motor with the speed reduction device.

The piston includes an extension extended therefrom, and a link coupled between the extension of the piston and the crank, to allow the piston to be moved by the motor and the crank. One or more batteries may be provided and coupled to the motor to energize the motor.

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Figure 1:
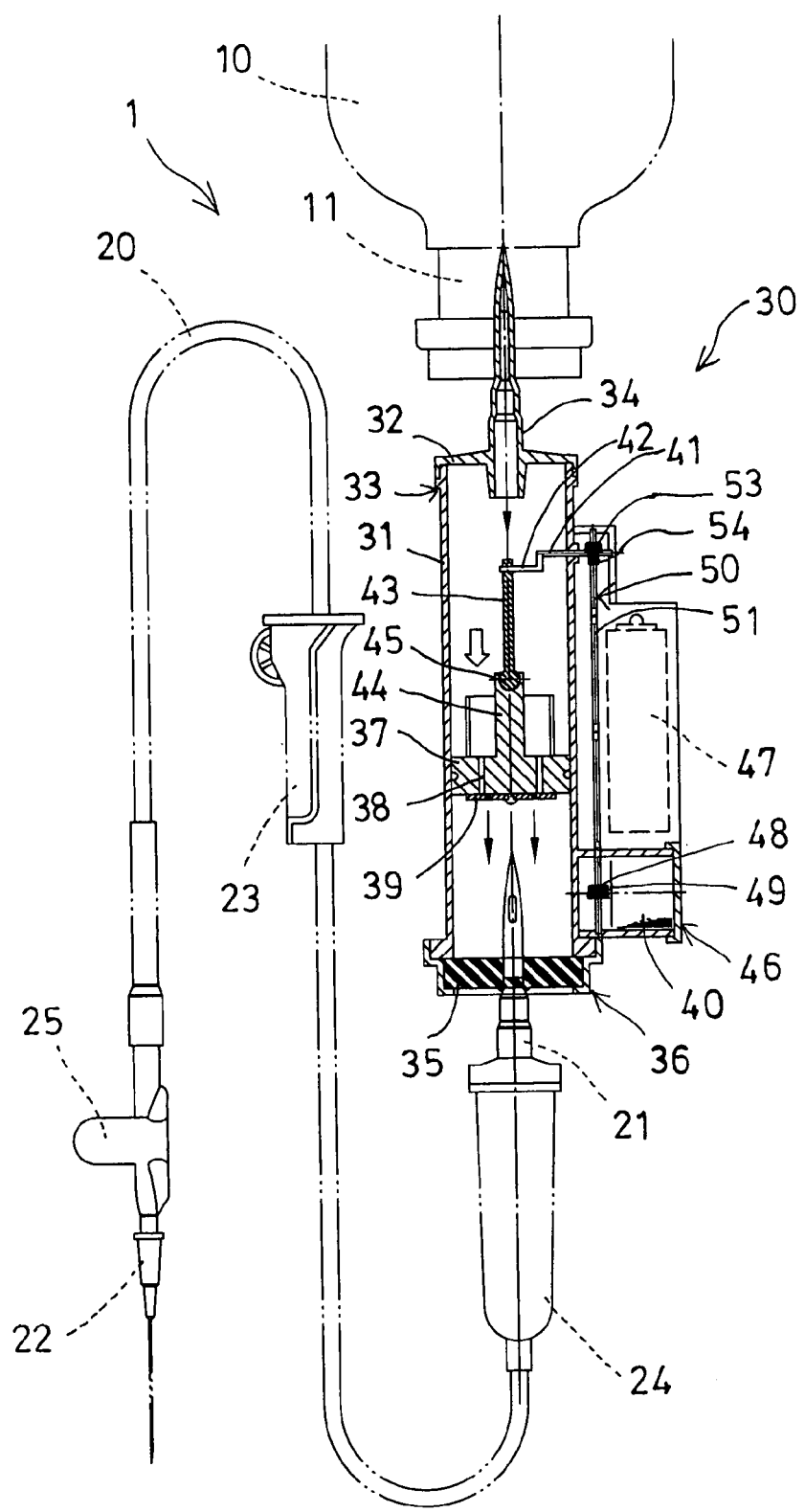
FIG. 1 is a partial cross sectional view of a fluid dispensing or feeding device in accordance with the present invention.
Figure 3:
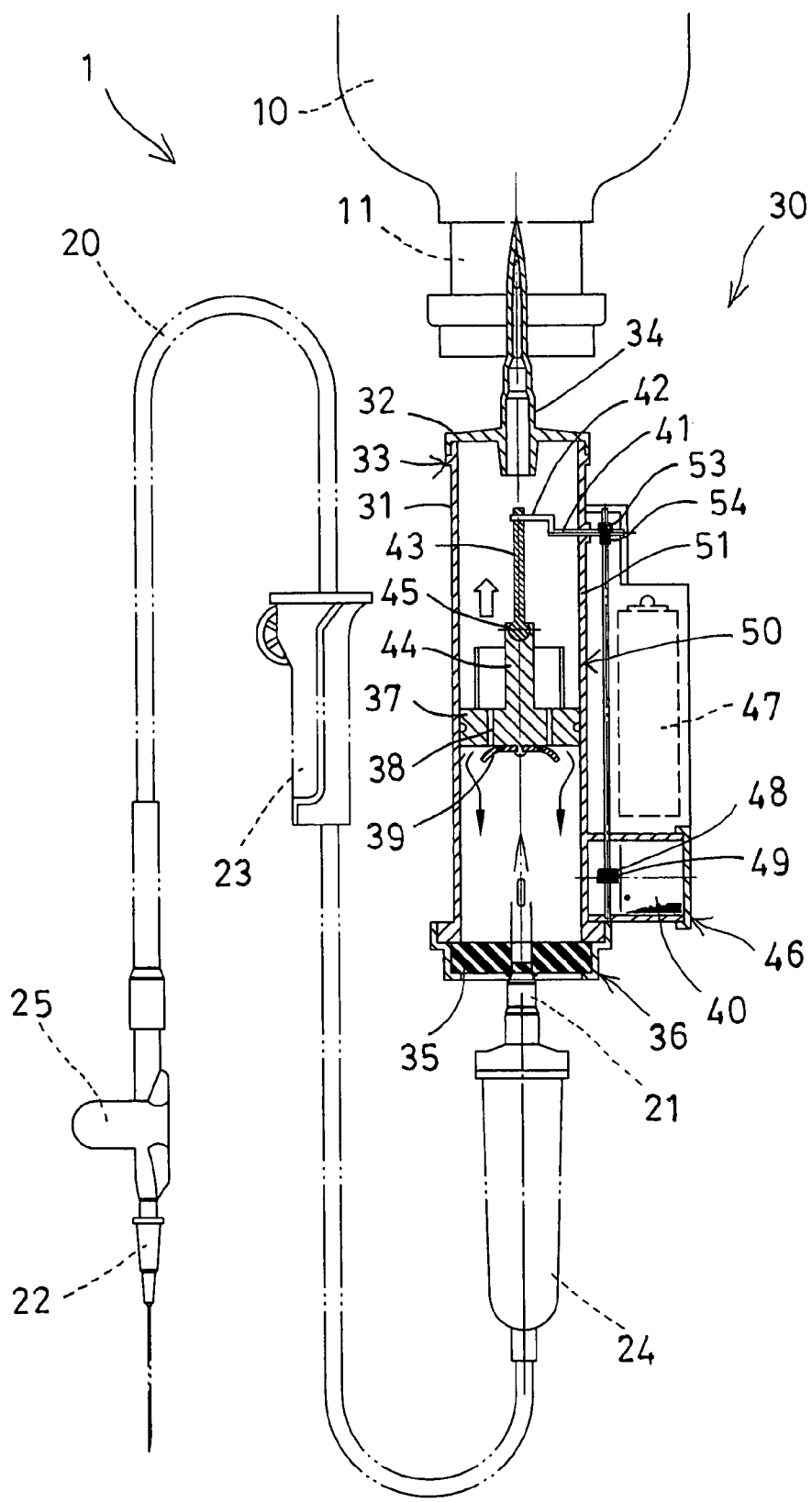
FIG. 3 is a partial cross sectional view similar to FIG. 1, illustrating the operation of the fluid dispensing or feeding device.

Referring to the drawings, and initially to FIGS. 1 and 3, a fluid dispensing or feeding device 1 in accordance with the present invention comprises a fluid container or bottle 10 for receiving fluids, such as medicinal fluids to be fed or injected intravenously into human body tissue, and a delivery or discharge tube 20 having a hollow hypodermic needle 21 provided on one end thereof for coupling to the bottle 10, and having an injection needle 22 provided on the other end thereof, for penetrating into patient's body tissue and for the purposes of injecting the fluid as desired. A clamp valve 23 is attached onto the flexible discharge tube 20 so as to control the dispensing or the rate of flow of the fluid in the well known manner.

Also positioned in the discharge tube 20 and located near the hollow hypodermic needle 21 or the bottle 10 is a drip meter or flow indicating device 24 usually made of transparent material for allowing the drops of fluid passing from the bottle 10 to the discharge tube 20 to be observed. An air relief valve 25 may further be provided and attached to the discharge tube 20, and preferably disposed close to the injection needle 22, for selectively relieving air, and for preventing air from being injected into human body tissue inadvertently, when no fluid is forced to flow through the discharge tube 20.

The fluid dispensing or feeding device 1 includes a pressurizing device 30 attached to or coupled between the bottle 10 and the discharge tube 20, for pressurizing the fluid and for allowing the fluid to flow through the discharge tube 20 despite of the gravity, and thus for allowing the fluid bottle 10 to be disposed below the hearts of the patients or users, and thus for allowing the fluid dispensing or feeding device 1 to be easily carried by the patients or users at any suitable position. The pressurizing means or device 30 includes a container 31 having a cap 32 attached to one end or portion 33 thereof, and a hollow hypodermic needle 34 provided on or attached onto or extended from the cap 32, for engaging into the bottle neck portion 11 of the bottle 10, and thus for receiving the fluid from the bottle 10.

The container 31 includes a resilient plug 35 attached to the other end or portion 36.thereof, for blocking or enclosing the other end or portion 36 of the container 31. The hollow hypodermic needle 21 of the discharge tube 20 is to be engaged through the resilient plug 35 and into the container 31, for allowing the fluid to flow out of the fluid container 31 and to flow through the discharge tube 20. The resilient plug 35 is preferably made of such as rubber or synthetic materials for resiliently clamping or engaging with the hollow hypodermic needle 21 and for making a water tight seal between the fluid container 31 and the hollow hypodermic needle 21.

The pressurizing device 30 further includes a piston 37 slidably received in the container 31, and having one or more passages 38 formed therein, and a valve member 39 in the form of rubber or resilient or spring panel 39 attached to the piston 37 and located closer to the plug 35, but distal to the cap 32, in order to selectively block the passages 38 of the piston 37, and so as to form a check valve, and to allow the piston 37 to force the fluid toward the plug 35 and into the discharge tube 20 via the hollow hypodermic needle 21 when the piston 37 is moved toward the plug 35 or away from the cap 32 (FIG. 1), and also to allow the fluid to flow through the passages 38 of the piston 37 when the piston 37 is moved away from the plug 35 or toward the cap 32 (FIG. 3).

A motor 40 is further provided and attached to the container 31, and a shaft 41 rotatably attached to or supported in the container 31 and extended into the container 31, and an eccentric crank 42 coupled to the shaft 41, for allowing the crank 42 to be rotated or driven by the shaft 41. A link 43 is pivotally or rotatably to the crank 42 (FIG. 2) and coupled to an extension 44 of the piston 37 with a pivot pin or universal joint 45, to allow the piston 37 to be moved or driven in a reciprocating action within the container 31 by the motor 40 and the shaft 41 and the crank 42. A coupling or connecting means or device or a speed reduction means or device or mechanism 50 is further provided and coupled between the motor 40 and the shaft 41 for allowing the shaft 41 to be rotated or driven by the motor 40 with a reduced driving speed and/or an increased driving torque.

For example, a casing 46 is provided on or attached onto or extended from the container 31 for receiving or supporting the motor 40 and/or one or more batteries 47 which may further be provided and coupled to the motor 40 in order to energize and actuate the motor 40. The motor 40 includes a pinion or worm or gear 48 attached to a spindle 49 thereof (FIGS. 1, 3). The speed reduction means or device 50 includes a pole 51 rotatably attached to or supported in the container 31 and preferably, but not necessarily arranged perpendicular to the pinion 48 and the shaft 41, and a worm or a gear 52 attached to one end of the pole 51 for engaging with the pinion 48 and thus for allowing the pole 51 and the gear 52 to be rotated or driven by the motor 40 with a reduced driving speed and/or an increased driving torque.

The speed reduction means or device 50 further includes a worm or a gear or a pinion 53 attached to the other end of the pole 51, and a further pinion or gear 54 attached to the shaft 41 and engaged with the pinion 53 of the pole 51 for allowing the shaft 41 and the crank 42 to be rotated or driven by the motor 40 with a reduced driving speed and/or an increased driving torque in order to move or actuate or operate the link 43 and the extension 44 and thus the piston 37 with a reduced driving speed and/or an increased driving torque.

In operation, as shown in FIG. 1, when the piston 37 is moved or driven toward the plug 35 or away from the cap 32 by the motor 40, the fluid contained in the lower portion 36 of the container 31 may be forced to flow toward the plug 35 and to flow into the discharge tube 20 via the hollow hypodermic needle 21, such that the fluid may be pressurized by the motor 40 and may be forced to flow through the discharge tube 20 without gravity, such that the fluid bottle 10 may be disposed below the hearts of the patients or users, and thus such that the fluid dispensing or feeding device 1 may be easily carried by the patients or users.

Figure 2:
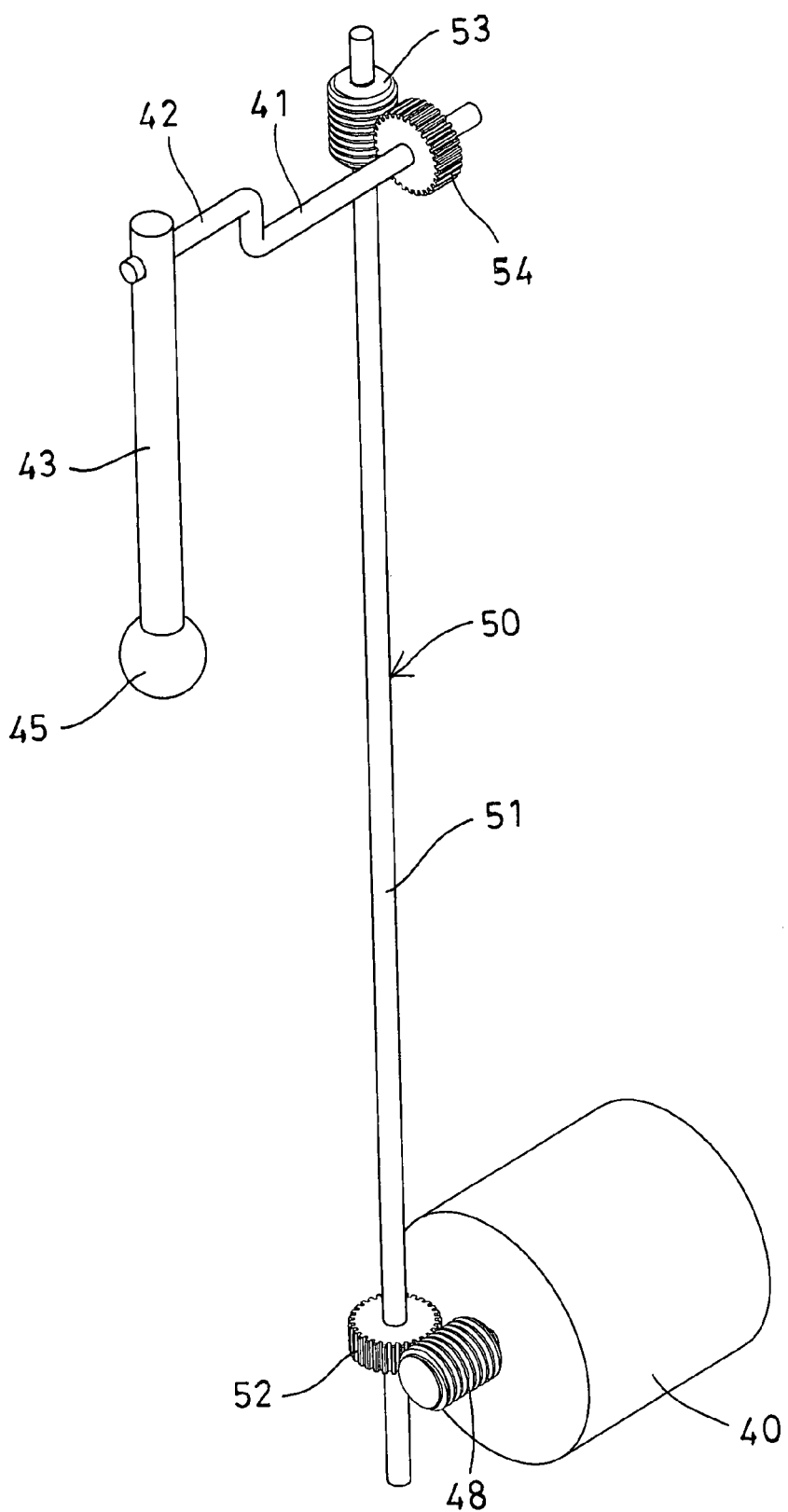
FIG. 2 is an enlarged partial perspective view of the fluid dispensing or feeding device.

As shown in FIG. 2, when the piston 37 is moved or driven away from the plug 35 or toward the cap 32 by the motor 40, the fluid contained in the upper portion 33 of the container 31 may flow through the passages 38 of the piston 37 and may then flow into the lower portion 36 of the container 31, for being forced to flow into the discharge tube 20 again when the piston 37 is moved or driven toward the plug 35 or away from the cap 32 by the motor 40 again, such that the fluid may be pressurized by the motor 40 in reciprocating action, and may be controlled and forced to flow through the discharge tube 20 without gravity.

The motor 40 and the piston 37 and/or clamp valve 23 and/or the flow indicating device 24 may be suitably arranged to control the dispensing or the rate of flow of the fluid through the discharge tube 20, and to prevent the fluid from being over pressurized. The motor 40 may be controlled or actuated by a switch (not shown) or the like, and the shaft 41 and the crank 42 and the piston 37 may be actuated or operated by the motor 40 and the speed reduction means or device 50 with a reduced driving speed and/or an increased driving torque for allowing the medicine fluid to be suitably injected into the patient's body tissue. The other control device (not shown) may be used to control or to adjust or to change the operating speed of the motor 40 and/or the rate of flow of the medicine fluid into the patient's body tissue.

Accordingly, the fluid dispensing or feeding device in accordance with the present invention includes a pressurizing device for pressurizing fluid and for allowing fluid bottle to be disposed below hearts of patients or users, and thus for allowing the fluid dispensing or feeding device to be easily carried by the patients or users, and includes a speed reduction device or mechanism coupled between the motor and the piston for allowing the piston to be actuated or driven by the motor with a reduced driving speed and/or an increased driving torque.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A fluid dispensing device comprising:
   a bottle for receiving fluid therein,
   a discharge tube,
   a pressurizing device coupled between said bottle and said discharge tube for pressurizing the fluid and for forcing the fluid to flow through said discharge tube without gravity,
   said pressurizing device including a container coupled between said bottle and said discharge tube, a piston slidably received in said container, and a motor coupled to said piston to move said piston in a reciprocating action within said container, and said container including a shaft rotatably supported in said container and extended into said container,
   an eccentric crank coupled to said shaft and coupled to said piston for allowing said piston to be driven by said shaft, and
   a speed reduction device coupled between said motor and said piston for allowing said piston to be actuated by said motor with a reduced driving speed.

2. The fluid dispensing device as claimed in claim 1, wherein said speed reduction device includes a first pinion attached to a spindle of said motor and coupled to said shaft for allowing said shaft to be driven by said motor.

3. The fluid dispensing device as claimed in claim 2, wherein said speed reduction device includes a pole rotatably supported in said container, a first gear attached to said pole and engaged with said first pinion, a second gear attached to said shaft, and a second pinion attached to pole and engaged with said second gear for allowing said shaft to be rotated and driven by said motor.

4. The fluid dispensing device as claimed in claim 1, wherein said piston includes an extension extended therefrom, and a link coupled between said extension of said piston and said crank, to allow said piston to be moved by said motor and said crank.

5. The fluid dispensing device as claimed in claim 1, wherein at least one battery is coupled to said motor to energize said motor.

* * * * *